United States Patent
Volk

(10) Patent No.: US 7,789,512 B2
(45) Date of Patent: Sep. 7, 2010

(54) REAL IMAGE FORMING EYE EXAMINATION LENS UTILIZING TWO REFLECTING SURFACES

(76) Inventor: Donald A. Volk, 3872 Owena St., Honolulu, HI (US) 96815

( * ) Notice: Subject to any disclaimer, the term of this patent is extended or adjusted under 35 U.S.C. 154(b) by 0 days.

(21) Appl. No.: 12/229,747

(22) Filed: Aug. 25, 2008

(65) Prior Publication Data

US 2009/0051872 A1    Feb. 26, 2009

Related U.S. Application Data

(60) Provisional application No. 60/966,109, filed on Aug. 23, 2007.

(51) Int. Cl.
*A61B 3/00* (2006.01)
*G02C 7/02* (2006.01)
*G02C 7/04* (2006.01)

(52) U.S. Cl. .................... 351/219; 351/160 R; 351/177

(58) Field of Classification Search ................ 359/219; 351/200, 205, 159, 160 R, 177, 219; 264/1.1, 264/1.9

See application file for complete search history.

(56) References Cited

U.S. PATENT DOCUMENTS 6,164,779 A    12/2000    Volk
7,144,111 B1    12/2006    Ross

*Primary Examiner*—Jack Dinh

(57) ABSTRACT

A diagnostic and therapeutic contact lens is provided for use with the slit lamp or other biomicroscope for the examination and treatment of the structures of the eye including that of the fundus and anterior chamber. The lens comprises a contacting portion adapted for placement on the cornea of an examined eye, two reflecting surfaces and a refracting portion. Light rays emanating from structures within the eye pass through the cornea and contacting portion of the lens and first reflect from the anterior reflecting surface as a positive reflection in a posterior direction. Following the first reflection the light rays reflect as a positive reflection in an anterior direction from the posterior reflecting surface to a refracting portion through which the light rays exit the lens. The lens focuses the light rays to produce a real image of the examined structures of the eye anterior of the lens or within the lens or element of the lens while optimally directing the light rays to the objective lens of the slit lamp or other biomicroscope for stereoscopic viewing and image scanning.

121 Claims, 4 Drawing Sheets

REAL IMAGE FORMING EYE EXAMINATION LENS UTILIZING TWO REFLECTING SURFACES

PRIORITY CLAIM

This application claims priority to U.S. Provisional Application Ser. No. 60/966,109 filed Aug. 23, 2007 and hereby incorporates that application by reference.

BACKGROUND OF THE INVENTION

1. Field of the Invention

The lens described in this disclosure relates to ophthalmoscopic lenses for use with the slit lamp or other biomicroscope. More particularly the invention relates to diagnostic and therapeutic gonioscopic and indirect ophthalmoscopic contact lenses that incorporate two reflecting surfaces which combine to provide positive power contributing to the formation of a real image of the examined structures of the eye anterior of the lens or within the lens or element of the lens while optimally directing the light rays to the objective lens of the slit lamp biomicroscope for stereoscopic viewing and image scanning.

2. Description of Prior Art

Eye examination lenses including indirect and direct ophthalmoscopy and gonioscopy lenses are used by ophthalmologists and optometrists for the diagnosis and treatment of the internal structures of the eye in conjunction with a slit lamp or other biomicroscope. Indirect ophthalmoscopy lenses, such as the Volk 90D lens, generally comprise a single lens with two refracting surfaces which combine to provide positive power contributing to the formation of a real image of the patient's eye fundus anterior of the examined eye. Direct ophthalmoscopy lenses, such as the Hruby lens, use minus power to produce a virtual image of the patient's eye fundus generally posterior of the examination lens. Some indirect and direct ophthalmoscopic lenses are pre-set or hand held in front of the patient's eye while others incorporate a contacting means and interface with the cornea and tear layer of the eye. An example of a contact indirect ophthalmoscopy lens would be the Volk QuadrAspheric lens and an example of a contact direct ophthalmoscopy lens would be the Volk Centralis Direct lens. Indirect ophthalmoscopy lenses provide a wide field inverted view while direct ophthalmoscopy lenses provide a small field with high magnification and high resolution in correct orientation.

Diagnostic lenses such as the Goldmann lens, Zeiss four mirror gonioscopy lens and Keoppe lens contact the eye and are used to examine and treat structures of the anterior chamber of the eye, specifically in the area of the anterior chamber angle, or iridocorneal angle. The four mirror lens incorporates angulated mirrors and like the other gonioscopy lenses operates to eliminate the power of the cornea to avoid total internal reflection of the light rays at the cornea-air interface. Light rays from the anterior chamber angle enter the lens and are reflected by mirrors along the line of vision of the viewer, one for each quadrant of the examined eye. In that a single mirror is used for each of the four sectional views, each image is reverted and discontinuous from the other sectional views. Furthermore the field of view obtainable through each mirror is very small. The Goldmann lens performs in an identical manner to the Zeiss four mirror lens except that it has only a single mirror used for gonioscopy. The Keoppe lens employs a contact lens having a rather highly curved convex anterior surface and a thickness sufficient to prevent total internal reflection of incident light rays from the anterior chamber angle from its convex surface, thereby allowing light rays to pass through for examination purposes. There is no real conjugate pupil formed by the Keoppe lens and the physician may only obtain a small field of view at an extremely angled inclination relative to the eye axis through a stereoscopic viewer.

Real image forming 'indirect ophthalmoscopic' viewing systems have also been suggested for viewing structures of the anterior chamber. An advantage of such a system lies in the continuous and uninterrupted field of view that may be provided in the form of an annular section corresponding to the structures of the anterior chamber angle, viewed with the slit lamp biomicroscope in its normal orientation. Such a system is described in U.S. Pat. No. 6,164,779 to Volk. This patent sets forth a series of lenses comprising a first corneal contacting lens system receiving light rays originating at the anterior chamber angle and a second imaging forming system receiving light rays from the first lens system producing a real image of the anterior chamber angle outside of the patient's eye. Various embodiments include refracting as well as reflecting surfaces providing positive power for focusing light rays. Although the U.S. Pat. No. 6,164,779 patent presents the first real image forming gonioscopy lens system of its day, the complexity of a number of embodiments as well as an insufficiency of others to provide correction of chromatic and other aberrations prevented commercialization of this invention. U.S. Pat. No. 7,144,111 to Ross, III, et al., represents an attempt to provide an improved real image forming gonioscopy lens. Although achromatized and corrected for other aberrations, the lenses depicted in the embodiments of the 111 patent exhibit numerous disadvantages that preclude its successful application, including excessive weight, an excessive lens length of over 35 mm, an excessive distance from the examined eye to the image plane of over 51 mm, which is beyond the positioning range of the slit lamp biomicroscope, and poor stereoscopic visualization and image scanning capability resulting from the small light ray footprint at the biomicroscope objective lens aperture.

SUMMARY OF THE INVENTION

Based on the foregoing there is found to be a need to provide a real image forming gonioscopy lens that avoids the problems associated with the prior art lenses and which in particular has improved optical quality and practicality of function and which avoids complexity of design and difficulty of manufacture. It is therefore a main object of the invention to provide an improved diagnostic and therapeutic gonioscopy lens that incorporates two reflecting surfaces that combine to provide positive power contributing to the formation of a real image.

It is another object of the invention to provide a diagnostic and therapeutic gonioscopy lens that provides a continuous and uninterrupted annular field of view.

It is another object of the invention to provide a diagnostic and therapeutic gonioscopy lens that is well corrected for optical aberrations including field curvature, astigmatic error and chromatic aberration.

It is another object of the invention to provide a diagnostic and therapeutic gonioscopy lens that provides an enhanced stereoscopic viewing capability, both during coaxial alignment of the biomicroscope with the lens as well as during scanning through movement of the biomicroscope.

It is another object of the invention to provide a diagnostic and therapeutic gonioscopy lens that comprises as few as one or two optical elements.

It is another object of the invention to provide a diagnostic and therapeutic indirect ophthalmoscopy lens that incorporates two reflecting surfaces that combine to provide positive power contributing to the formation of a real image.

It is another object of the invention to provide a diagnostic and therapeutic indirect ophthalmoscopy lens that provides a continuous and uninterrupted annular field of view of the peripheral retina.

These and other objects and advantages are accomplished by a diagnostic and therapeutic eye examination lens that incorporates two reflecting surfaces that work in concert to provide positive power contributing to the formation of a real image. By appropriately pairing an anterior reflector with a posterior plus powered reflector optical aberrations thereby may be reduced and the lens corrected to a very high degree. The optical materials selected and curvatures provided result in a lens with improved optical quality, practicality of function and simplicity of design.

The lens described in this disclosure functions as both a condensing lens, directing light from the illumination portion of a biomicroscope to the visualized eye structures, and an image forming lens, producing a real image of the illuminated eye structures in an image plane anterior of the examined eye. The light pathways through the lens are folded through the use of two reflecting surfaces that optimally correct optical aberrations while shortening the distance to the plane of the real image.

The ophthalmoscopic contact lenses described in this disclosure may be used for general diagnosis as well as for treatment by means of the delivery of laser energy to the trabecular meshwork and adjacent iris structures of the eye, i.e., laser trabeculoplasty, peripheral laser iridoplasty, laser iridotomy, and in the delivery of laser energy in the treatment of the equatorial and peripheral retina. The term "ophthalmoscopic contact lens" as used in this disclosure refers to a contact lens for diagnosis or laser treatment of the interior structures of the eye including those of the fundus within the posterior chamber and the iris and iridocorneal angle within the anterior chamber.

In the lens described in this disclosure light rays proceeding through the lens from the examined eye to the real image first reflect as a positive reflection in a posterior direction from the anterior reflecting surface and following the first reflection reflect as a positive reflection in an anterior direction from the posterior reflecting surface. A 'positive' reflection is herein defined as a reflected light ray, originating from the examined eye, which proceeds from the point of reflection further from the optical axis of the lens than the incident ray as determined by the point of intersection of each with a perpendicular to the axis of the lens. Conversely, a 'negative' reflection is defined as a reflected light ray, originating from the examined eye, which proceeds from the point of reflection closer to the optical axis of the lens than the incident ray as determined by the point of intersection of each with a perpendicular to the axis of the lens. By posterior direction is meant a direction towards or closer to the examined eye with reference to the Z axis component or direction of the propagating light rays, the Z axis being known to those skilled in the art as defining the coordinate dimension along or parallel to the optical axis of the lens. By anterior direction is meant a direction away or further from the examined eye with reference to the Z axis component or direction of the propagating light rays.

The inventor has found that by using positive reflections in the stated posterior and anterior directions diagnostic and therapeutic lenses incorporating such surfaces with specific curvature and shape attributes may combine with other lens features to avoid aberrations often associated with optical systems incorporating curved surfaces reflecting oblique incident light rays, and to provide excellent optical quality with a minimum of elements and/or surfaces.

In some embodiments a single element consisting of two reflecting and refracting surfaces may comprise the entire lens. In other embodiments an additional lens element may be incorporated to minimize spot size and alter the beam footprint at the biomicroscope objective lens aperture, for example.

The lens may be produced of either a polymeric material such as polymethylmethacrylate (pmma), polycarbonate, polystyrene, ally diglycol carbonate (CR-39®) or any other suitable polymeric material or any glass material, for example N-BK7 (available from Schott AG) and S-LAH64, S-LAH58 or S-FPL51 (available from Ohara Corporation) or other glass type.

In the lens described in this disclosure the surface that comprises the anterior reflector and the refracting portion surrounding it may comprise a continuous aspheric curvature, wherein both the reflecting and refracting portions are defined by the same surface parameters as a single curvature. Alternatively the surface may comprise a lenticular surface, wherein the reflecting portion and the refracting portion each are defined by different surface parameters as different curvatures. The anterior reflector surface may be concave, plano or convex, and if aspheric may comprise a polynomial-defined aspheric surface with both concave and convex attributes.

In embodiments comprising a cemented doublet, wherein the anterior surface of the interface comprises a refracting portion that adjoins the posterior reflector, the mating interface surfaces may define concave, plano or convex curvatures, thereby providing a contacting element that is bi-concave, plano-concave or meniscus in shape.

The level of correction of chromatic aberration obtainable with the lens is outstanding. As the reflecting surfaces together provide significant positive power contributing to the formation of the real image, the refracting surfaces may be tailored to minimize or practically eliminate dispersion.

Scanning of the real image may be accomplished by lateral and vertical movement of the biomicroscope and in conjunction with angulation or tilting of the gonioscopy lens on the eye the visualized area may be expanded to include a larger extent of the iris and the inner corneal surface adjacent the iridocorneal angle.

Other features and advantages of the invention will become apparent from the following description of the invention in conjunction with the accompanying drawings.

BRIEF DESCRIPTION OF THE DRAWINGS

FIG. 2b shows a more detailed view of the light ray pathways illustrated in FIG. 2a.

DETAILED DESCRIPTION

Figure 1:
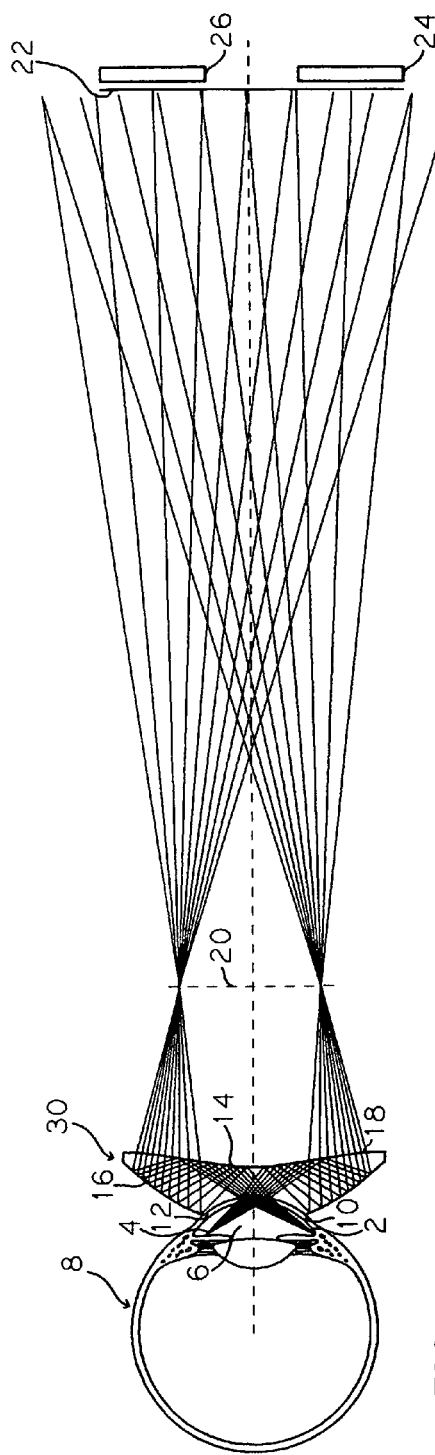
FIG. 1 shows the lens layout and ray tracing of a single element gonioscopy lens according to a first embodiment of the invention.

Referring to FIG. 1, there is shown a ray tracing and schematic cross-sectional view of a lens layout of an exemplary single element gonioscopy lens 30 according to a first embodiment of the invention. Lens 30 is small in diameter, lightweight and incorporates refracting surfaces that are balanced to minimize chromatic aberration. The real image produced by this lens is well within the range of motion of the slit lamp biomicroscope and the view provided is stereoscopic across the entire visualized field. The lens is made of optical quality polymethylmethacrylate with an index of refraction of approximately Nd=1.492 and an Abbe number of approximately Vd=55.3. Alternatively, the lens may be made of N-BK7 glass, having an index of refraction of approximately Nd=1.517 and an Abbe number of approximately Vd=64.2. The two lenses have identical design and prescription values with the plastic lens offering greater ease of manufacture and the glass lens offering enhanced scratch resistance, durability and sterilization capability. In practice the lens is mounted in a holding frame or housing and applied to the cornea of a patient's eye in a manner similar to that used in conjunction with gonioscopic prisms and indirect ophthalmoscopic contact lenses and which is generally know to those skilled in the art. For ease of illustration the frame is not included in the present or subsequent figures.

For illustrative purposes, only two rays are shown emanating from point sources on opposite sides of the optical axis of the lens within the anterior chamber of the schematic eye. Light ray pathway 2 represents an iridocorneal point source and light ray pathway 4 represents a mid-peripheral iris point source. Referring to FIG. 1, light rays 2 and 4 emanating from the stated iridocorneal and mid-peripheral iris locations of anterior chamber 6 of schematic eye 8 pass through the cornea 10 and tear layer (not shown) of the eye and enter gonioscopy lens 30 through corneal contacting surface 12 and proceed to reflecting surface 14 where they are reflected in a posterior and positive direction towards reflecting surface 16. The light rays reflect from mirror surface 16 in an anterior and positive direction towards surface 18 where they are refracted and focus at real image plane 20 anterior of lens 30. The rays proceed towards biomicroscope objective lens aperture 22 and enter left and right microscope lenses 24 and 26, respectively, of the observing stereomicroscope. The stereomicroscope is adjusted to focus at real image plane 20 to provide an inverted view of the observed structures of the eye.

As can be seen in FIG. 1 the ray span of both light bundles 2 and 4 at the plane of biomicroscope aperture 22 exceeds the extent of the biomicroscope aperture and the left and right microscope lenses 24 and 26, thus insuring binocular and stereoscopic biomicroscope visualization of the observed image both when the biomicroscope is coaxial with the lens as shown and when the biomicroscope is moved off axis to bring peripheral image points to a more central location of the visual field of the biomicroscope. The ray spans of lenses depicted in subsequent figures and embodiments likewise exceed the extent of the biomicroscope aperture and the left and right microscope lenses.

Illumination of the anterior chamber structures may be provided by the slit lamp biomicroscope's illumination system in a typical manner. The par focal illumination system will provide light to the anterior chamber following similar light ray pathways as shown, from the image plane back through the lens and cornea to the anterior chamber.

Figure 2B:
Figure 2A:
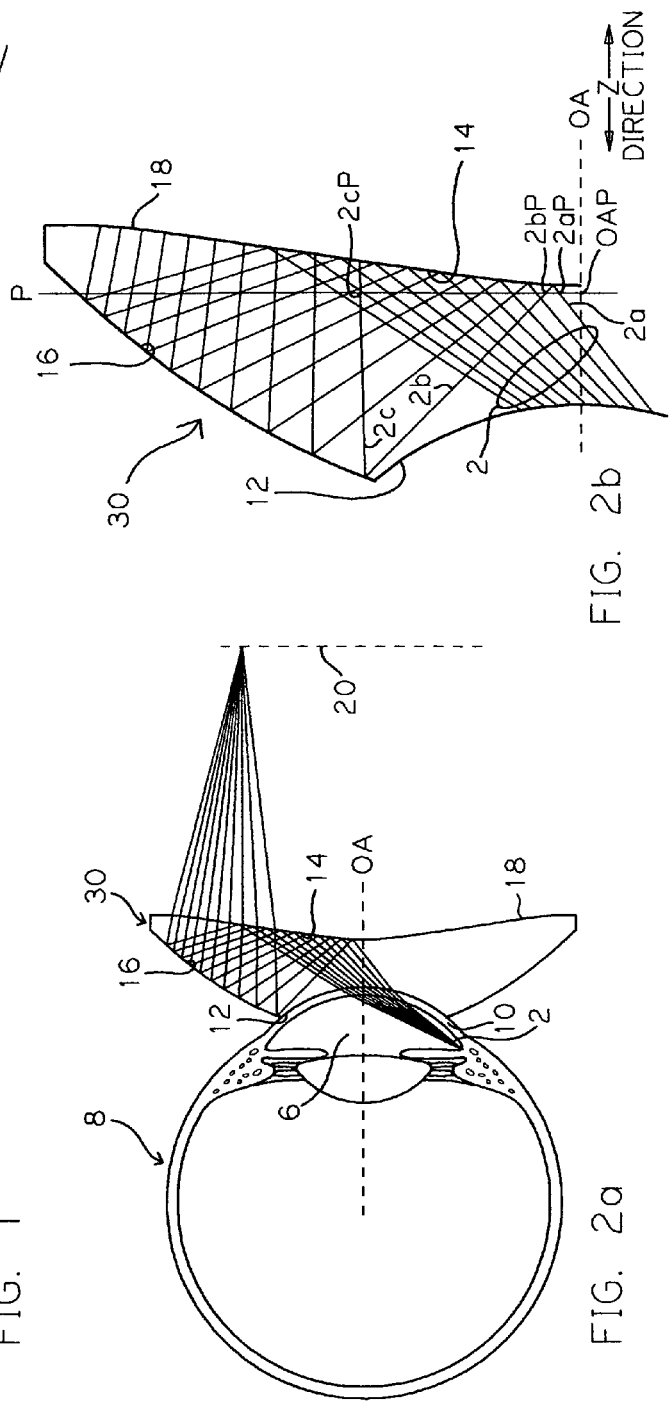
FIG. 2a shows a detailed view of the lens of FIG. 1.

FIG. 2a shows the same lens as in FIG. 1 minus light ray 4 and minus the diverging rays proceeding from lens element 30 to the plane of the biomicroscope, in order to better illustrate the light pathway directions and lens surfaces. In fact, numerous light rays will pass through the lens to focus in the image plane and be viewed through the biomicroscope, including all rays proceeding from illuminated points of the uninterrupted annular section comprising the entire anterior chamber angle, mid-peripheral and peripheral iris and inner corneal surface in the vicinity of the iridocorneal angle. For ease of illustration, the tear film, referenced above, is not shown in the present or subsequent figures. As previously described, light ray 2 emanating from the iridocorneal angle of anterior chamber 6 of eye 8 passes through the cornea 10 and tear layer of the eye and enters lens 30 through corneal contacting surface 12 and proceeds to reflecting surface 14 where it is reflected in a posterior and positive direction towards reflecting surface 16. The light ray reflects from mirror surface 16 in an anterior and positive direction towards surface 18 where they are refracted and focus at real image plane 20 anterior of lens 30.

Contacting surface 12 comprises a concave surface adapted for placement on the patient's cornea, and interfaces with the cornea through the tear film or an interface solution as is commonly used with diagnostic and therapeutic contact lenses. The corneal contacting surface of the lens described in this disclosure may have a spherical or aspherical curvature. In the exemplary lens of this embodiment contacting surface 12 has an aspheric curvature. Reflecting surface 14 and refracting surface 18 comprise a single continuous aspheric curvature as the anterior surface of the lens, with a portion of surface 14 that provides reflection through total internal reflection serving also as a portion of refracting surface 18 for light rays exiting the lens contributing to the formation of the real image. Refracting surface 18 and reflecting surface 14 comprise a rotationally symmetric polynomial aspheric surface having both positive and negative power attributes. Refracting surface 18 in concert with the other lens surfaces focuses light rays at the plane of the real image. Reflecting surface 14 provides an internally reflecting surface reflecting light rays directed to it from corneal contacting surface 12 in a posterior direction. Reflecting surface 14 may be mirror coated over an area up to 9.5 mm in diameter, and at a minimum may be 3.2 mm in diameter. In the exemplary lens of this embodiment the mirror coating extends to 4 mm in diameter, beyond which light rays that reflect will do so through total internal reflection (TIR). Total internal reflection of light rays in polymethylmethacrylate occurs when the incident light ray angle exceeds approximately 42 degrees and occurs in N-BK7 glass when the incident light ray angle exceeds approximately 41.4 degrees, the values of which correspond to the minimum 3.2 mm diameter stated above.

Reflecting surface 16 is disposed posterior of reflecting surface 14 and together with contacting surface 12 comprises a lenticulated surface as the posterior surface of the lens. Reflecting surface 16 provides an internally reflecting concave curvature and therefore provides plus power to the lens, converging light rays directed to it from reflecting surface 14. Reflecting surface 16 comprises a mirror-coated annular section having a 9.2 mm inner diameter that surrounds contacting surface 12. The mirrored portion of surface 14 and mirrored surface 16 may be mirrored by means of vacuum deposition of an evaporated or sputtered metal such as aluminum or silver, and protectively overcoated with a hardcoating, polymer or paint layer, as is known to those skilled in the art. The formula:

$$z = \frac{cr^2}{1 + \sqrt{1 - (1+k)c^2 r^2}} + a_1 r + a_2 r^2 + a_3 r^3 \ldots a_n r^n.$$

has been utilized in defining the aspheric surfaces of this invention, where z equals the surface sag along the lens axis, c equals the curvature (i.e., reciprocal of the radius), r is the radial coordinate in lens units, k equals the conic constant, and $a_n$ (where n=1, 2, . . . ) is the coefficient value of any of the selected conic deformation terms.

As previously mentioned, in the lens described in this disclosure light rays proceeding through the lens from the examined eye to the real image first reflect as a positive reflection in a posterior direction from the anterior reflecting surface and following the first reflection reflect as a positive reflection in an anterior direction from the posterior reflecting surface. A 'positive' reflection is a reflected light ray, originating from the examined eye, which proceeds from the point of reflection further from the optical axis of the lens than the preceding incident ray as determined by the point of intersection of each with a perpendicular to the axis of the lens. FIG. 2b shows an enlargement of the portion of lens 30 that contains the pathway of light ray bundle 2 depicted in FIG. 2a, proceeding through the lens from contacting surface 12 to final refracting surface 18, clearly illustrating the individual rays of light ray bundle 2 conforming to the prescription of positive reflection as described. Line P is perpendicular to lens axis OA and OAP represents the point of intersection of line P and lens axis OA. Referring to FIG. 2b, individual reflected light ray 2b of ray bundle 2 proceeds from anterior reflector surface 14 further from lens axis OA than preceding incident ray 2a as demonstrated by each ray's respective intersection point 2bP and 2aP with line P and specifically as demonstrated by the greater distance from 2bP to OAP compared to the lesser distance from 2aP to OAP. Reflected light ray 2c proceeds from posterior reflector surface 16 further from lens axis OA than ray 2b, which in this case is the incident ray, as demonstrated by each ray's respective intersection point 2cP and 2bP with line P and specifically as demonstrated by the greater distance of 2cP to point OAP compared to the lesser distance of 2bP to OAP. All light rays emanating from the area of the iridocorneal angle and peripheral iris reflect in this manner in the present all well as in subsequent embodiments and examples of the invention. Any perpendicular line to the lens axis that intersects any pair of incident and reflected rays will demonstrate this property.

The prescription for the exemplary lenses of this embodiment is provided in the tables below. For the present and subsequent exemplary lenses "CC" denotes a surface with a concave apical radius and "CX" denotes a surface with a convex apical radius with respect to reflected or refracted rays incident up the surface of the designated Material in the table. For the Material 'air', the curvature is with respect to the listed material type of the preceding table row. The values for some numbers have been rounded.

| Surface | Material | Apical radius | Conic constant | Thickness mm | Diameter mm |
|---|---|---|---|---|---|
| 12 | pmma | −6.0 cc | −2.0 | 3.729 | 9.2 |
| 14 | mirror/pmma | 11.799 cx | −38.950 | −6.057 | 27 |
| 16 | mirror/pmma | 13.78 cc | −1.265 | 6.057 | 27 |
| 18 image | air | 11.799 cc | −38.950 | 21.73 | 27 |

| Surface | Coefficient r2 | Coefficient r4 | Coefficient r6 | Coefficient r8 |
|---|---|---|---|---|
| 12 | | | 1.95e−005 | −1.05e−006 |
| 14 & 18 | .00326528 | −4.47658e−005 | 3.216303e−007 | −1.010986e−009 |
| 16 | −.0003023 | −1.33631e−006 | 1.103433e−007 | −3.241906e−010 |

Prescription for Exemplary Lenses of the First Embodiment

Figure 3:
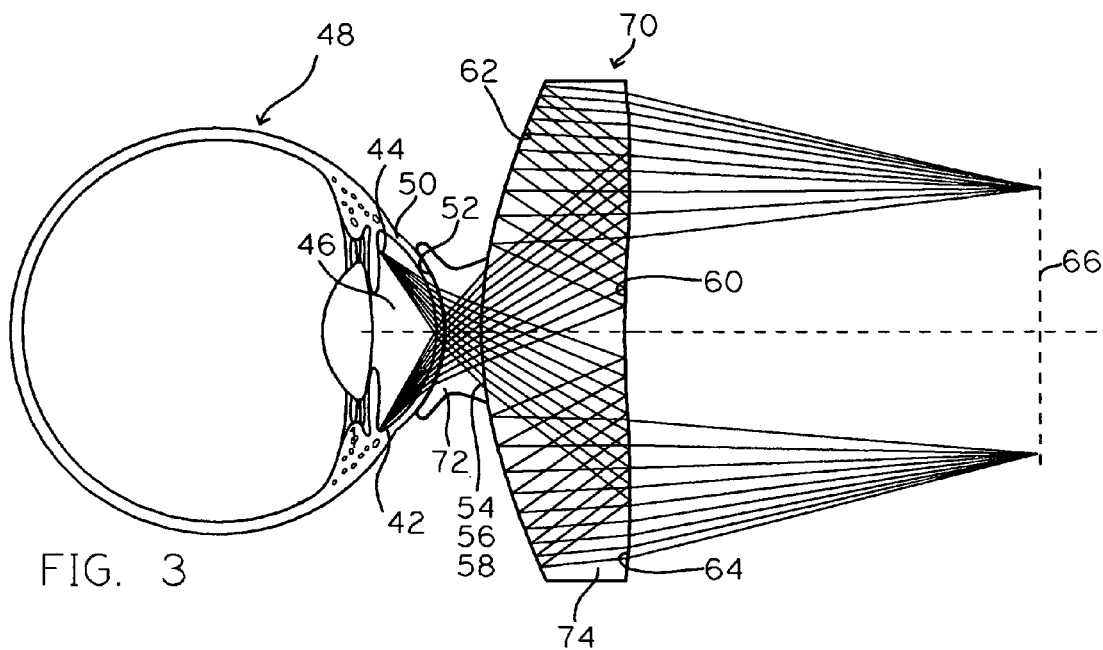
FIG. 3 shows the lens layout and ray tracing of a cemented doublet gonioscopy lens according to a second embodiment of the invention.

Referring to FIG. 3, there is shown a schematic cross-sectional view of a lens layout of an exemplary doublet gonioscopy lens according to a second embodiment of the invention, wherein lens 70 comprises a cemented lens including posterior element 72 and anterior element 74. The lens provides a high magnification image exhibiting low chromatic error.

Posterior element 72 is made of optical quality polycarbonate having an index of refraction of approximately Nd=1.585 and an Abbe number of approximately Vd=29.9 and anterior element 74 is made of S-LAH64, having an index of refraction of approximately Nd=1.788 and an Abbe number of approximately Vd=47.4. The two element 72 and 74 are glued together at their interface using a suitable optical adhesive such as NOA 68 or NOA 78 (available from Norland Products).

Referring to FIG. 3, light rays 42 and 44 emanating from the stated iridocorneal and mid-peripheral iris locations of anterior chamber 46 of schematic eye 48 pass through the cornea 50 and tear layer of the eye and enter posterior element 72 of lens 70 through corneal contacting surface 52 and continue through cemented interface 54, comprised of (refracting) surfaces 56 and 58 respectively of lens elements 72 and 74 bonded together by the optical cement, into anterior lens element 74 and to reflecting surface 60 where they are reflected in a posterior and positive direction towards reflecting surface 62. The light rays reflect from mirror surface 62 in an anterior and positive direction towards surface 64 where they are refracted and focus at real image plane 66 anterior of lens 70. The biomicroscope may be adjusted by the practitioner to focus at real image plane 66 to provide an inverted view of the observed structures of the eye.

Contacting surface 52 comprises a concave aspheric surface adapted for placement on the patient's cornea. Interface 54 is the cemented interface of substantially matching but oppositely curved mating surfaces 56 and 58. Reflecting surface 60 and refracting surface 64 comprise a single continuous aspheric curvature as the anterior surface of lens element 74, with a portion of surface 60 that provides reflection through total internal reflection serving also as a portion of refracting surface 64 for light rays exiting the lens contributing to the formation of the real image. Refracting surface 64 and reflecting surface 60 comprise a rotationally symmetric polynomial aspheric surface having both positive and negative power attributes. Refracting surface 64 in concert with the other lens surfaces focuses light rays at the plane of the real image. Reflecting surface 60 provides an internally reflecting surface reflecting light rays directed to it from corneal contacting surface 52 in a posterior direction. Reflecting surface 60 is mirror coated over an area 12 mm in diameter, beyond which light rays that reflect will do so through total internal reflection (TIR). Total internal reflection of light rays in S-LAH64 glass occurs when the incident light ray angle exceeds approximately 34 degrees, the value of which corresponds a minimum semi-diameter value of 6 mm.

Reflecting surface 62 is disposed posterior of reflecting surface 60 and together with surface 58 comprises a continuous aspheric surface as the posterior surface of the lens element 74. Reflecting surface 62 provides an internally reflecting concave curvature and therefore provides plus power to the lens, converging light rays directed to it from reflecting surface 60. Reflecting surface 62 comprises a mirror-coated annular section having a 8 mm inner diameter that surrounds refracting surface area 58. The mirrored portion of surface 60 and mirrored surface 62 may be mirrored and protectively overcoated by means previously described.

As can be seen in FIG. 3 the contacting end 52 of posterior element 72 has been shaped to provide function as an eyelid flange. An eyelid flange facilitates a positive interface with the tear or fluid layer of the eye when the patient tends to blink or squeeze the eyelids closed during the diagnostic or treatment procedure, and the use of such a flange is known to those skilled in the art. The contacting surfaces and elements of the prior and subsequent figures and embodiments likewise may incorporate diameters or recesses that provide a lid flange function, only some of which are shown in the figures.

The prescription for the exemplary lens of this embodiment is provided in the tables below.

| Surface | Material | Apical radius | Conic constant | Thickness mm | Diameter mm |
|---|---|---|---|---|---|
| 52 | polycarbonate | 7.7 cc | −.18 | 2.117 | 8.5 |
| 58 | S-LAH64 | .1313 cx | −7575.1 | 8.774 | 8 |
| 60 | mirror/S-LAH64 | 33.631 cx | −45.693 | −8.774 | 31 |
| 62 | mirror/S-LAH64 | .1313 cc | −7575.1 | 8.774 | 31 |
| 64 | air | 33.631 cc | −45.693 | 24.00 | 31 |
| image | | | | | |

| Surface | Coefficient r2 | Coefficient r4 | Coefficient r6 | Coefficient r8 |
|---|---|---|---|---|
| 58 & 62 | .0178350 | −2.345026e−006 | −3.691509e−008 | 3.1492318e−011 |
| 60 & 64 | −.0041956 | −1.540027e−005 | 1.2995703e−008 | 3.5710653e−011 |

Prescription for Exemplary Lens of the Second Embodiment

Figure 4:
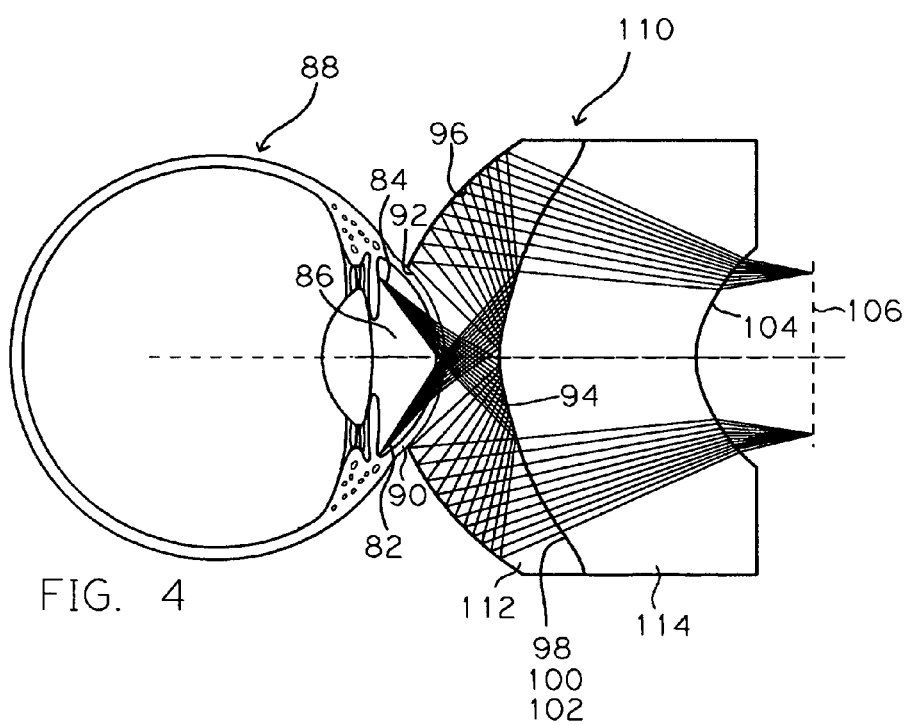
FIG. 4 shows the lens layout and ray tracing of a cemented doublet gonioscopy lens according to third embodiment of the invention.

Referring to FIG. 4, there is shown a schematic cross-sectional view of a lens layout of an exemplary doublet gonioscopy lens according to a third embodiment of the invention, wherein lens 110 comprises a cemented lens including posterior element 112 and anterior element 114. The lens provides sharp imaging characteristics at a slightly reduced magnification and provides protection of the anterior mirrored surface by way of embedment at the cemented interface.

Posterior element 112 is made of optical quality polymethylmethacrylate having an index of refraction of approximately Nd=1.492 and an Abbe number of approximately Vd=55.3 and anterior element 114 is made of optical quality polycarbonate, having an index of refraction of approximately Nd=1.585 and an Abbe number of approximately Vd=29.9. The two elements 112 and 114 are glued together at their interface using a suitable optical adhesive as previously described.

Referring to FIG. 4, light rays 82 and 84 emanating from the stated iridocorneal and mid-peripheral iris locations of anterior chamber 86 of schematic eye 88 pass through the cornea 90 and tear layer of the eye and enter posterior element 112 of lens 110 through corneal contacting surface 92 and proceed to reflecting surface 94 where they are reflected in a posterior and positive direction towards reflecting surface 96. The light rays reflect from mirror surface 96 in an anterior and positive direction and continue through cemented interface 98, comprised of (refracting) surfaces 100 and 102 respectively of lens elements 112 and 114 bonded together by the optical cement, into anterior lens element 114. The light rays proceed in their respective directions towards surface 104 where they exit the lens, focus at real image plane 106 and continue towards the biomicroscope. The biomicroscope may be adjusted by the practitioner to focus at real image plane 106 to provide an inverted view of the observed structures of the eye.

Contacting surface 92 comprises a concave aspheric surface adapted for placement on the patient's cornea. Reflecting surface 94 and refracting surface 100 comprise a single continuous polynomial aspheric curvature as the anterior surface of lens element 112. Reflecting surface 94 provides an internally reflecting convex curvature diverging light rays directed to it from corneal contacting surface 92. Reflecting surface 94 is mirror coated over an area 10.8 mm in diameter, and reflects light rays contributing to the formation of the real image from this mirrored portion only.

Reflecting surface 96 is disposed posterior of reflecting surface 94 and together with contacting surface 92 comprises a lenticulated surface, with both reflecting surface 96 and contacting surface 92 comprising aspheric surfaces, the two surfaces together forming the posterior surface of lens element 112. Reflecting surface 96 provides an internally reflecting concave curvature and therefore provides plus power to the lens, converging light rays directed to it from reflecting surface 94. Reflecting surface 96 comprises a mirror-coated annular section having an 11.1 mm inner diameter that surrounds contacting surface area 92. Mirrors 94 and 96 may be mirrored and protectively overcoated by means previously described. Cemented interface 98 is the cemented interface of substantially matching but oppositely curved mating surfaces 100 and 102.

The prescription for the exemplary lens of this embodiment is provided in the tables below.

| Surface | Material | Apical radius | Conic constant | Thickness mm | Diameter mm |
|---|---|---|---|---|---|
| 92 | pmma | 6.8 cc | −2.5 | 3.25 | 11 |
| 94 | mirror/pmma | 7.971 cx | −31.043 | −6.7 | 23 |
| 96 | mirror/pmma | 12.178 cc | −.4399 | 6.7 | 26 |
| 100 | pmma/cement | 7.971 cc | −31.043 | .2 | 23 |
| 102 | polycarbonate | 7.971 cx | −31.043 | 11.9 | 23 |
| 104 | air | 12.138 cc | 1.6272 | 7 | 14 |
| image | | | | | |

| Surface | Coefficient r2 | Coefficient r4 | Coefficient r6 | Coefficient r8 |
|---|---|---|---|---|
| 92 | | | −2.3e−005 | 2.8e−007 |
| 94 | .017891 | −.00017575 | 2.54704e−006 | −8.98673e−009 |
| 96 | −.0038515 | −5.930989e−006 | −7.244304e−008 | −5.3549224e−012 |
| 100 & 102 | .017891 | −.00017575 | 2.54704e−006 | −8.98673e−009 |
| 104 | .0603864 | −.0017645 | 3.153828e−005 | −2.4193825e−007 |

Prescription for Exemplary Lens of the Third Embodiment

FIG. 4 is also referenced with regard to additional exemplary lenses of the same embodiment wherein reflection of incident light rays occurs by means of mirroring as well as by TIR. TIR may be accomplished by either lowering the refractive index of the optical cement or by both lowering the refractive index of the optical cement and increasing the refractive index of posterior lens element 112.

The second exemplary lens comprises posterior lens element 112 and anterior lens element 114 having the same material composition and the optical cement of interface 98 having a refractive index of 1.35 (Opti-Clad, available from Optical Polymer Research, Inc). Reflecting surface 94 is mirror coated to 10.5 mm in diameter, beyond which incident light rays will reflect through TIR.

The prescription for the second exemplary lens is provided in the tables below.

| Surface | Material | Apical radius | Conic constant | Thickness mm | Diameter mm |
|---|---|---|---|---|---|
| 92 | pmma | 6.8 cc | −2.5 | 3.25 | 11 |
| 94 | mirror/pmma | 7.971 cx | −31.043 | −6.7 | 23 |
| 96 | mirror/pmma | 12.178 cc | −.4399 | 6.7 | 26 |
| 100 | pmma/cement | 7.971 cc | −31.043 | .2 | 23 |
| 102 | polycarbonate | 7.971 cx | −31.043 | 12.2 | 23 |
| 104 image | air | 12.138 cc | 1.6272 | 7 | 14 | having a refractive index of 1.40 (Opti-Clad, available from Optical Polymer Research, Inc.), and anterior lens element 114 also made of polycarbonate. Reflecting surface 94 is mirror coated to 9.6 mm in diameter, beyond which incident light rays will reflect through TIR.

The prescription for the third exemplary lens is provided in the tables below.

| Surface | Material | Apical radius | Conic constant | Thickness mm | Diameter mm |
|---|---|---|---|---|---|
| 92 | polycarbonate | 7.0 cc | −2.0 | 3.25 | 11 |
| 94 | mirror/polycarb | 7.971 cx | −31.043 | −6.6 | 23 |
| 96 | mirror/polycarb | 12.178 cc | −.4399 | 6.6 | 26 |
| 100 | polycarb/cement | 7.971 cc | −31.043 | .2 | 23 |
| 102 | polycarbonate | 7.971 cx | −31.043 | 11.8 | 23 |
| 104 image | air | 13.0 cc | 1.6272 | 6.6 | 14 |

| Surface | Coefficient r2 | Coefficient r4 | Coefficient r6 | Coefficient r8 |
|---|---|---|---|---|
| 92 | | | −2.3e−005 | 2.8e−007 |
| 94 | .017891 | −.00017575 | 2.54704e−006 | −8.98673e−009 |
| 96 | −.0038515 | −5.930989e−006 | −7.244304e−008 | −5.3549224e−012 |
| 100 & 102 | .017891 | −.00017575 | 2.54704e−006 | −8.98673e−009 |
| 104 | .0603864 | −.0017645 | 3.153828e−005 | −2.4193825e−007 |

Prescription for 2$^{nd}$ Exemplary Lens of the Third Embodiment

The third exemplary lens comprises posterior lens element 112 made of optical quality polycarbonate, an optical cement

| Surface | Coefficient r2 | Coefficient r4 | Coefficient r6 | Coefficient r8 |
|---|---|---|---|---|
| 92 | | | −1.5e−005 | 1e−007 |
| 94 | .017891 | −.00017575 | 2.54704e−006 | −8.98673e−009 |
| 96 | −.0038515 | −5.930989e−006 | −7.244304e−008 | −5.3549224e−012 |
| 100 & 102 | .017891 | −.00017575 | 2.54704e−006 | −8.98673e−009 |
| 104 | .0603864 | −.0017645 | 3.153828e−005 | −2.4193825e−007 |

Prescription for 3rd Exemplary Lens of the Third Embodiment

Figure 5:
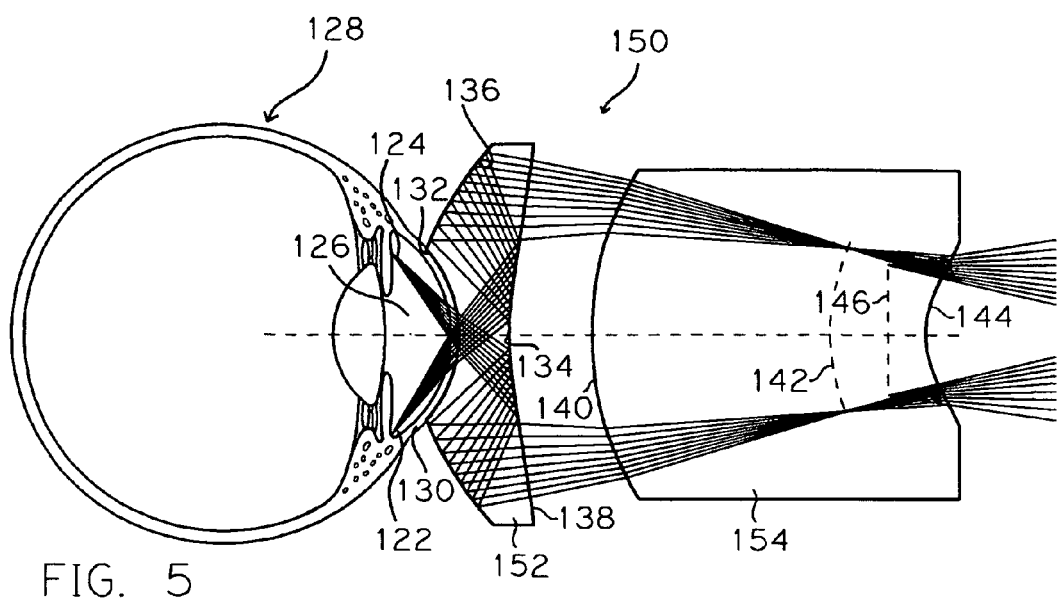
FIG. 5 shows the lens layout and ray tracing of a two element air-spaced gonioscopy lens according to a fourth embodiment of the invention.

Referring to FIG. 5, there is shown a schematic cross-sectional view of a lens layout of an exemplary two element gonioscopy lens according to a fourth embodiment of the invention, wherein lens 150 comprises an air spaced lens including posterior element 152 and anterior element 154, and wherein the real image is formed within anterior lens element 154.

Posterior element 152 is made of optical quality polymethylmethacrylate and anterior element 154 is made of S-FPL51 glass having an index of refraction of approximately Nd=1.497 and an Abbe number of approximately Vd=81.5. The two elements 152 and 154 are in a spaced apart relationship comprising an air gap.

Referring to FIG. 5, light rays 122 and 124 emanating from the stated iridocorneal angle and mid-peripheral iris locations of anterior chamber 126 of eye 128 pass through the cornea 130 and tear layer of the eye and enter lens element 152 through corneal contacting surface 132 and proceed to reflecting surface 134 where they are reflected in a posterior and positive direction towards reflecting surface 136. The light rays reflect from mirror surface 136 in an anterior and positive direction towards surface 138 where they are refracted, exit lens element 152 and proceed towards lens element 154. The light rays enter lens element 154 through surface 140 and focus at real image 142 and continue to surface 144 where they exit the lens and proceed to the biomicroscope. The biomicroscope may be adjusted by the practitioner to focus at virtual image plane 146 to provide an inverted view of the observed structures of the eye.

Contacting surface 132 comprises a concave aspheric surface adapted for placement on the patient's cornea. Reflecting surface 134 and refracting surface 138 comprise a single continuous aspheric curvature as the anterior surface of lens element 152, with a portion of surface 134 that provides reflection through total internal reflection serving also as a portion of refracting surface 138 for light rays exiting the lens contributing to the formation of the real image. Refracting surface 138 and reflecting surface 134 comprise a rotationally symmetric polynomial aspheric surface having both positive and negative power attributes. Refracting surface 138 in concert with the other lens surfaces of lens element 152 optimally directs light rays to lens element 154. Reflecting surface 134 provides an internally reflecting surface reflecting light rays directed to it from corneal contacting surface 132 in a posterior direction. Reflecting surface 134 may be mirror coated over an area up to 15.5 mm in diameter, and at a minimum may be 4 mm in diameter. In the exemplary lens of this embodiment the mirror coating extends to 5 mm in diameter, beyond which light rays that reflect will do so through total internal reflection (TIR).

Reflecting surface 136 is disposed posterior of reflecting surface 134 and together with contacting surface 132 comprises a lenticulated surface, with both reflecting surface 134 and contacting surface 132 comprising aspheric surfaces, the two surfaces together forming the posterior surface of lens element 152. Reflecting surface 136 provides an internally reflecting concave curvature and therefore provides plus power to the lens, converging light rays directed to it from reflecting surface 134. Reflecting surface 136 comprises a mirror-coated annular section having a 10.4 mm inner diameter that surrounds contacting surface area 132. Mirrors 134 and 136 may be mirrored and protectively overcoated by means previously described. Surfaces 140 and 142 of anterior lens element 154 are both aspheric surfaces.

The prescription for the exemplary lens of this embodiment is provided in the tables below.

| Surface | Material | Apical radius | Conic constant | Thickness mm | Diameter mm |
|---|---|---|---|---|---|
| 132 | pmma | 7.7 cc | −.18 | 3.031 | 10.3 |
| 134 | mirror/pmma | 12.646 cx | −53.460 | −5.967 | 22 |
| 136 | mirror/pmma | 13.519 cc | −1.187 | 5.967 | 23 |
| 138 | air | 12.646 cc | −53.460 | 5 | 22 |
| 140 | S-FPL51 | 18.0 cx | .8357 | 14.2 | 20 |
| image | S-FPL51 | | | 5.8 | |
| 144 | air | 8.0 cc | −1.740 | | 11.2 |

| Surface | Coefficient r2 | Coefficient r4 | Coefficient r6 | Coefficient r8 |
|---|---|---|---|---|
| 134 | .0029341 | −3.655345e−005 | 3.607101e−007 | −1.4815665e−009 |
| 136 | 9.034102e−017 | 1.304715e−006 | 1.001129e−007 | −2.896274e−010 |
| 140 | −.0064358 | .0001160 | −1.502486e−006 | 4.4219206e−009 |
| 144 | .02762382 | −.0005595 | −9.57932e−006 | 1.9244686e−007 |

Prescription for Exemplary Lens of the Fourth Embodiment

Figure 6:
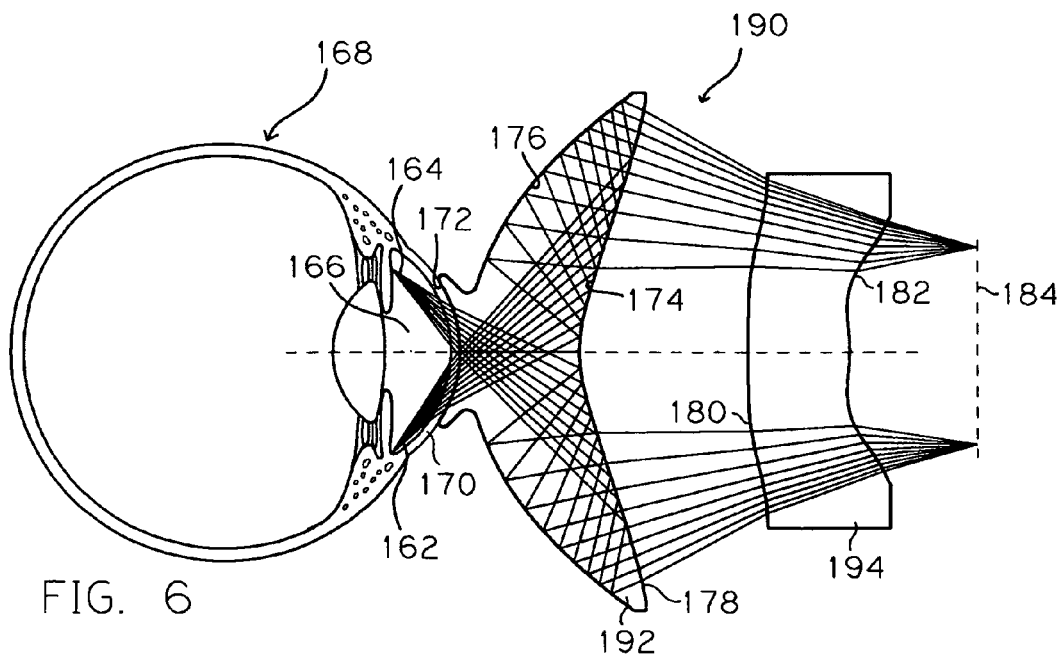
FIG. 6 shows the lens layout and ray tracing of a two element air-spaced gonioscopy lens according to a fifth embodiment of the invention.

Referring to FIG. 6, there is shown a schematic cross-sectional view of a lens layout of an exemplary two element gonioscopy lens according to a fifth embodiment of the invention, wherein lens 190 comprises an air spaced lens including posterior element 192 and anterior element 194, and wherein the real image is formed anterior of anterior lens element 194. The posterior reflecting surface is spaced 2 mm away from the examined eye at its closet point and as such provides excellent motility of the lens within the orbital area of the eye.

Both posterior element 192 and anterior element 194 are made of optical quality polymethylmethacrylate. The two elements 192 and 194 are in a spaced apart relationship comprising an air gap.

Referring to FIG. 6, light rays 162 and 164 emanating from the stated iridocorneal angle and mid-peripheral iris locations of anterior chamber 166 of eye 168 pass through the cornea 170 and tear layer of the eye and enter lens element 192 through corneal contacting surface 172 and proceed to reflecting surface 174 where they are reflected in a posterior and positive direction towards reflecting surface 176. The light rays reflect from mirror surface 176 in an anterior and positive direction towards surface 178 where they are refracted, exit lens element 192 and proceed towards lens element 194. The light rays enter lens element 194 through surface 180 and continue to surface 182 where they exit the lens and focus at real image 184 from which they continue to the biomicroscope. The biomicroscope may be adjusted by the practitioner to focus at real image plane 184 to provide an inverted view of the observed structures of the eye.

Contacting surface 172 comprises a concave aspheric surface adapted for placement on the patient's cornea. Reflecting surface 174 and refracting surface 178 comprise a single continuous aspheric curvature as the anterior surface of lens element 192, with a portion of surface 174 that provides reflection through total internal reflection serving also as a portion of refracting surface 178 for light rays exiting the lens contributing to the formation of the real image. Refracting surface 178 and reflecting surface 174 comprise a rotationally symmetric polynomial aspheric surface having both positive and negative power attributes. Refracting surface 178 in concert with the other lens surfaces optimally directs light rays to lens element 194. Reflecting surface 174 provides an internally reflecting surface reflecting light rays directed to it from corneal contacting surface 172 in a posterior direction. Reflecting surface 174 may be mirror coated over an area up to 9.8 mm in diameter, and at a minimum may be 4.6 mm in diameter. In the exemplary lens of this embodiment the mirror coating extends to 5 mm in diameter, beyond which light rays that reflect will do so through total internal reflection (TIR).

Reflecting surface 176 is disposed posterior of reflecting surface 174 and comprises an aspheric curvature. Reflecting surface 176 provides an internally reflecting concave curvature and therefore provides plus power to the lens, converging light rays directed to it from reflecting surface 174. Reflecting surface 176 comprises a mirror-coated annular section having an 8 mm inner diameter that surrounds contacting surface area 172. Mirrors 174 and 176 may be mirrored and protectively overcoated by means previously described. Surfaces 180 and 182 of anterior lens element 194 are both higher order aspheric surfaces.

Figure 7:
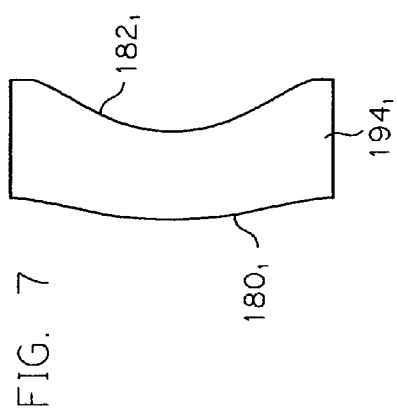
FIG. 7 shows an alternate design of the lens of the fifth embodiment

FIG. 7 shows an alternative design to anterior lens element 194 with surfaces 180₁ and 182₁ of alternative anterior lens element 194₁ having identical refractive characteristics to surfaces 180 and 182 respectively with regard to light rays contributing to the formation of the real image, yet being free from severe curvature inflections thus providing a continuity of curvature lending itself to conventional methods of manufacture.

The prescription for the exemplary lens of this embodiment is provided in the tables below.

| Surface | Material | Apical radius | | Conic constant | Thickness mm | Diameter mm |
|---|---|---|---|---|---|---|
| 172 | pmma | 7.7 | cc | −.18 | 7.064 | 8.5 |
| 174 | mirror/pmma | 7.034 | cx | −5.1721 | −6.685 | 30 |
| 176 | mirror/pmma | 7.950 | cc | −1.393 | 6.685 | 31 |
| 178 | air | 7.034 | cc | −5.1721 | 10 | 30 |
| 180 | pmma | 17.154 | cx | .88948 | 6 | 21.4 |
| 182 image | air | 7.732 | cx | −.25956 | 7.476 | 16 |

Prescription for Exemplary Lens of the Fifth Embodiment

Figure 8:
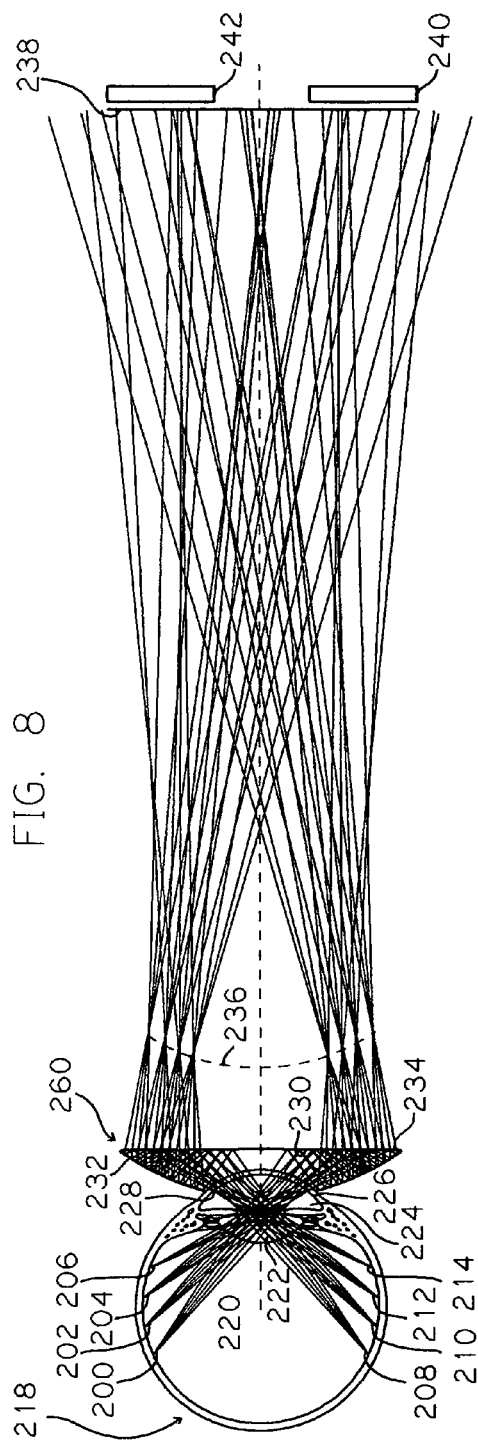
FIG. 8 shows the lens layout and ray tracing of a single element indirect ophthalmoscopy contact fundus lens according to a sixth embodiment of the invention.

Referring to FIG. 8, there is shown a ray tracing and schematic cross-sectional view of an exemplary single element indirect ophthalmoscopy contact lens 260 according to a sixth embodiment of the invention. The lens receives light rays from points in the peripheral fundus and through refraction and reflection means similar to that of prior embodiments focuses the rays to form a real image as a continuous and uninterrupted annular section anterior of the examined eye. This lens provides an unusually wide field of view of the peripheral fundus at a high magnification. Lens 260 is made of optical quality polymethylmethacrylate.

Referring to FIG. 8, light rays 200, 202, 204, 206, 208, 210, 212 and 214 emanating from equatorial-to-peripheral retinal sections of eye 218 pass through the vitreous humor 220, crystalline lens 222, anterior chamber 224, cornea 226 and tear layer of the eye and enter lens 260 through contacting surface 228 and continue to concave mirror surface 230 where they are reflected in a posterior and positive direction towards concave mirror surface 232. The light rays reflect from mirror surface 232 in an anterior and positive direction towards refracting surface 234 where they exit the lens and focus at real image plane 236 anterior of lens 260. The rays proceed towards biomicroscope objective lens aperture 238 and enter left and right microscope lenses 240 and 242, respectively, of the observing stereomicroscope. The stereomicroscope may be adjusted by the practitioner to focus at real image plane 236 to provide an inverted view of the observed structures of the eye.

In a manner similar to the prior gonioscopy lens embodiments light rays 200 to 214 emanating from the fundus of eye 218 span an area at the plane of biomicroscope objective lens 238 that exceeds the extent of the biomicroscope aperture and the left and right microscope lenses 240 and 242, thus insuring binocular and stereoscopic biomicroscope visualization of the observed image both when the biomicroscope is coaxial with the lens as shown and when the biomicroscope is moved off axis to bring peripheral image points to a more central location of the visual field of the biomicroscope.

Figure 9:
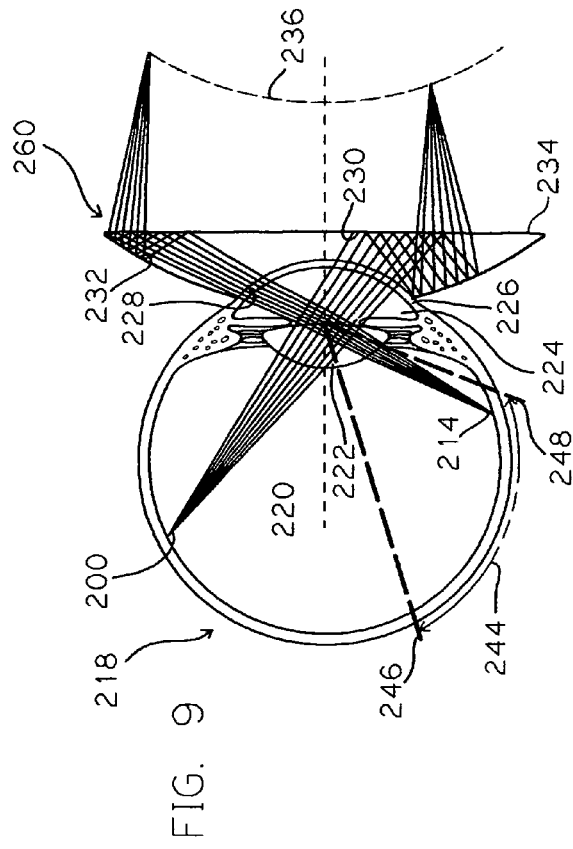
FIG. 9 shows a detailed view of the lens of FIG. 8

FIG. 9 shows a more detailed lens layout and ray tracing of the same lens shown in FIG. 7 with the exception that only two light rays are shown so that each light ray pathway may be more easily identified. Light rays 200 and 214 emanate from points in the equatorial and peripheral retinal regions of eye 218 at 35 degrees and 60 degrees respectively in relation to the anterior surface of crystalline lens 222. In terms of field angles within the eye as measured from the center of the globe, wherein, for example, a point on the equator is considered to be at a 90 degree location and an equator to equator extent of fundus represents a 180 degree field angle, light ray 200 emanates from a 59.6 degree location and light ray 214 emanates from a 99.3 degree location. The field extent of the annular section viewable as represented by the two rays there-

| Surface | Coefficient r2 | Coefficient r4 | Coefficient r6 | Coefficient r8 |
|---|---|---|---|---|
| 174 & 178 | −.0093 | 3.6336915e−006 | 4.6708732e−008 | −2.2175482e−010 |
| 176 | −.0253221 | 8.667446e−005 | −3.900806e−008 | −1.297222e−010 |
| 180 | −.02971832 | .00046843 | −5.878946e−006 | 1.6606586e−008 |
| 182 | −.112222 | .00402582 | −6.7422955e−005 | 3.0020947e−007 | fore ranges from 119.2 degrees to 198.6 degrees. With the lens described in this disclosure it is possible to view an even greater extent of fundus, although the most extreme angles viewable may be monocular due to vignetting or oblique passage of light rays through the eye pupil. A maximum viewable field extent is represented by the section along curved line 244 between broken lines 246 and 248, which spans from central fundus to peripheral fundus locations. The field extent of the annular section represented by curved line 246, as measured from the center of the globe, ranges from 58.6 degrees to 224.4 degrees.

Referring to the FIG. 9, light rays 200 and 214 emanate from points in the equatorial and peripheral retina and pass through the vitreous humor 220, crystalline lens 222, anterior chamber 224, cornea 226 and tear layer of the eye and enter lens 260 through contacting surface 228 and continue to concave mirror surface 230 where they are reflected in a posterior and positive direction towards concave mirror surface 232. The light rays reflect from mirror surface 232 in an anterior and positive direction towards refracting surface 234 where they exit the lens and focus at real image plane 236 anterior of lens 260.

Contacting surface 228 comprises a concave aspheric surface adapted for placement on the patient's cornea. Reflecting surface 230 and refracting surface 234 comprise a single continuous aspheric curvature as the anterior surface of lens element 260, with a portion of surface 230 that provides reflection through total internal reflection serving also as a portion of refracting surface 234 for light rays exiting the lens contributing to the formation of the real image. Refracting surface 234 and reflecting surface 230 comprise a rotationally symmetric polynomial aspheric surface having both positive and negative power attributes. Refracting surface 234 in concert with the other lens surfaces focuses light rays at the plane of the real image. Reflecting surface 230 provides an internally reflecting concave surface converging light rays directed to it from corneal contacting surface 228 and directing them in a posterior direction towards reflecting surface 232. Reflecting surface 230 may be mirror coated over an area up to 11.8 mm in diameter, and at a minimum may be 9.7 mm in diameter. In the exemplary lens of this embodiment the mirror coating extends to 11.8 mm in diameter, beyond which light rays that reflect will do so through total internal reflection (TIR). Reflecting surface 230 may be mirrored over the stated 11.8 mm diameter extent or alternatively its central 4 mm diameter area may be non-mirrored, thus creating an annular mirror section and providing a central aperture through which the central fundus may be viewed with the biomicroscope.

Reflecting surface 232 is disposed posterior of reflecting surface 230 and together with contacting surface 228 comprises a lenticulated surface, with both reflecting surface 232 and contacting surface 228 comprising aspheric surfaces, the two surfaces together forming the posterior surface of lens 260. Reflecting surface 232 provides an internally reflecting concave curvature and therefore provides plus power to the lens, converging light rays directed to it from reflecting surface 230.

The prescription for the exemplary lens of this embodiment is provided in the tables below.

| Surface | Material | Apical radius | Conic constant | Thickness mm | Diameter mm |
|---|---|---|---|---|---|
| 228 | pmma | 7.116 cc | −.84746 | 2 | 11.25 |
| 230 | mirror/pmma | 75.693 cc | −1707.46 | −5 | 28 |

-continued

| Surface | Material | Apical radius | Conic constant | Thickness mm | Diameter mm |
|---|---|---|---|---|---|
| 232 | mirror/pmma | 23.5 cc | .4787 | 5 | 28 |
| 234 | air | 75.693 cc | −1707.46 | 11 to 15 | 28 |
| image | | | | | |

| Surface | Coefficient r4 | Coefficient r6 | Coefficient r8 |
|---|---|---|---|
| 228 | −7.653385e−006 | 6.734311e−007 | −8.800456e−009 |
| 230 & 234 | −1.716917e−006 | 1.030831e−008 | −2.006143e−011 |
| 232 | −5.602171e−006 | −1.830799e−008 | −1.069211e−010 |

Prescription for Exemplary Lens of the Sixth Embodiment

The invention has been described in detail with respect to various embodiments and it will now be apparent from the foregoing to those skilled in the art that changes and modifications may be made without departing from the invention in its broader aspects. For example, the embodiments describing lenses presented in this disclosure made of particular glass or plastic materials may instead be made with other polymers or with other optical glass having any refractive index and Abbe value. It should be further understood that materials such as high temperature polymers suitable for optical applications may be used as replacements for acrylic or polycarbonate in order to accommodate high temperature sterilization procedures. Furthermore, as mentioned with respect to the first embodiment, glass may be used instead of plastic to provide enhanced scratch resistance, durability and sterilization capability. It should be further understood that the curvatures of two surfaces optically cemented together at the optical interface of a doublet cemented lens need not have exactly the same curvature and may have different curvatures. As a further modification, additional lens elements may be incorporated into any of the embodiment designs without departing from the scope of the invention. Furthermore, the anterior surface that both reflects as well as refracts light rays proceeding from the illuminated point sources as depicted in the various layouts may be lenticulated, reflecting light rays from a central portion of one particular curvature and refracting light rays from a peripheral annular portion of a different curvature, the surface having a juncture point where the two curvatures meet or joining without discontinuity. Furthermore, any of the embodiments may incorporate a transparent or light filtering glass or plastic protective cover, and any refracting surfaces may be coated with an anti-reflective coating to lessen glaring reflection. It should be further understood that the aspheric curves described for each embodiment are only representative, and that the nature of a lens surface may change according to the particular design of the biomicroscope or instrument used to capture the light rays as well as the refractive status of the examined eye. It should be further understood that the indirect ophthalmoscopy lens of the seventh embodiment may comprise a cemented lens, a two element lens, have a plurality of elements or be made of a different material type than described with reference to the exemplary lens. Furthermore, the lenses of each embodiment may be modified to provide a direct view of the eye fundus through a non-mirrored center portion of the lens where mirroring does not provide reflection of light rays contributing to the formation of the real image, thereby providing a light transmitting aperture centrally over the optical axis of the lens. Additionally, it should be understood that the lenses described in this disclosure may be used in conjunction with an instrument other than a biomicroscope, such as an image capturing device, as a digital camera or digital image storing device, and that the illumination source may be other than that of a standard full wavelength white light illumination source, for example, the illumination may comprise light of monochromatic wavelengths or may comprise a laser or scanning laser, and that the capture system may be appropriate for such monochromatic or laser or laser scanned light, as is known to those skilled in the art. The invention, therefore, as defined in the appended claims is intended to cover all such changes and modifications as fall within the true spirit of the invention.

What is claimed is:

1. An opthalmoscopic contact lens for viewing or treating structures within an eye, comprising:
    a contacting surface adapted for placement on a cornea of an eye;
    an anterior reflecting surface positioned anterior of the contacting surface;
    a posterior reflecting surface positioned posterior of the anterior reflecting surface; and
    a refracting surface positioned anterior to the posterior reflecting surface;
    wherein light rays emanating from structures within the eye enter the lens through the contacting surface and are each reflected in an ordered sequence of reflections first as a positive reflection in a posterior direction by the anterior reflecting surface and next as a positive reflection in an anterior direction by the posterior reflecting surface, and
    further wherein the light rays pass through the refracting surface to form an inverted final real image of the structures.

2. The opthalmoscopic contact lens of claim 1, wherein the structures are structures within an anterior chamber of the eye.

3. The opthalmoscopic contact lens of claim 1, wherein the posterior reflecting surface is at least partially concave.

4. The opthalmoscopic contact lens of claim 3, wherein the posterior reflecting surface is at least partially mirrored.

5. The opthalmoscopic contact lens of claim 4, wherein curvature of the anterior reflecting surface is at least partially plano.

6. The opthalmoscopic contact lens of claim 5, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

7. The opthalmoscopic contact lens of claim 6, wherein the anterior reflecting surface and the refracting surface together comprise a continuous surface.

8. The opthalmoscopic contact lens of claim 6, wherein the opthalmoscopic contact lens is a doublet lens.

9. The opthalmoscopic contact lens of claim 8, wherein the doublet lens is a cemented doublet lens that includes
    an anterior portion; and
    a posterior portion that includes the contacting surface and an opposing surface opposite the contacting surface;
    wherein curvature of the opposing surface is a curvature selected from the group consisting of at least partially plano, at least partially concave, and at least partially convex.

10. The opthalmoscopic contact lens of claim 4, wherein curvature of the anterior reflecting surface is at least partially concave.

11. The opthalmoscopic contact lens of claim 10, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

12. The opthalmoscopic contact lens of claim 11, wherein the anterior reflecting surface and the refracting surface together comprise a continuous surface.

13. The opthalmoscopic contact lens of claim 11, wherein the opthalmoscopic contact lens is a doublet lens.

14. The opthalmoscopic contact lens of claim 13, wherein the doublet lens is a cemented doublet lens that includes
    an anterior portion; and
    a posterior portion that includes the contacting surface and an opposing surface opposite the contacting surface;
    wherein curvature of the opposing surface is a curvature selected from the group consisting of at least partially plano, at least partially concave, and at least partially convex.

15. The opthalmoscopic contact lens of claim 4, wherein curvature of the anterior reflecting surface is at least partially convex.

16. The opthalmoscopic contact lens of claim 15, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

17. The opthalmoscopic contact lens of claim 16, wherein the anterior reflecting surface and the refracting surface together comprise a continuous surface.

18. The opthalmoscopic contact lens of claim 16, wherein the opthalmoscopic contact lens is a doublet lens.

19. The opthalmoscopic contact lens of claim 18, wherein the doublet lens is a cemented doublet lens that includes
    an anterior portion; and
    a posterior portion that includes the contacting surface and an opposing surface opposite the contacting surface;
    wherein curvature of the opposing surface is a curvature selected from the group consisting of at least partially plano, at least partially concave, and at least partially convex.

20. The opthalmoscopic contact lens of claim 4, wherein curvature of the anterior reflecting surface is at least partially a polynomial-defined curvature that includes concave and convex attributes.

21. The opthalmoscopic contact lens of claim 20, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

22. The opthalmoscopic contact lens of claim 21, wherein the anterior reflecting surface and the refracting surface together comprise a continuous surface.

23. The opthalmoscopic contact lens of claim 21, wherein the opthalmoscopic contact lens is a doublet lens.

24. The opthalmoscopic contact lens of claim 23, wherein the doublet lens is a cemented doublet lens that includes
    an anterior portion; and
    a posterior portion that includes the contacting surface and an opposing surface opposite the contacting surface;

wherein curvature of the opposing surface is a curvature selected from the group consisting of at least partially plano, at least partially concave, and at least partially convex.

25. The opthalmoscopic contact lens of claim 1, wherein the structures are structures within a posterior chamber of the eye.

26. The opthalmoscopic contact lens of claim 25, wherein the posterior reflecting surface is at least partially concave.

27. The opthalmoscopic contact lens of claim 26, wherein the posterior reflecting surface is at least partially mirrored.

28. The opthalmoscopic contact lens of claim 27, wherein curvature of the anterior reflecting surface is at least partially plano.

29. The opthalmoscopic contact lens of claim 28, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

30. The opthalmoscopic contact lens of claim 29, wherein the anterior reflecting surface and the refracting surface together comprise a continuous surface.

31. The opthalmoscopic contact lens of claim 29, wherein the opthalmoscopic contact lens is a doublet lens.

32. The opthalmoscopic contact lens of claim 31, wherein the doublet lens is a cemented doublet lens that includes
   an anterior portion; and
   a posterior portion that includes the contacting surface and an opposing surface opposite the contacting surface;
   wherein curvature of the opposing surface is a curvature selected from the group consisting of at least partially plano, at least partially concave, and at least partially convex.

33. The opthalmoscopic contact lens of claim 27, wherein curvature of the anterior reflecting surface is at least partially concave.

34. The opthalmoscopic contact lens of claim 33, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

35. The opthalmoscopic contact lens of claim 34, wherein the anterior reflecting surface and the refracting surface together comprise a continuous surface.

36. The opthalmoscopic contact lens of claim 34, wherein the opthalmoscopic contact lens is a doublet lens.

37. The opthalmoscopic contact lens of claim 36, wherein the doublet lens is a cemented doublet lens that includes
   an anterior portion; and
   a posterior portion that includes the contacting surface and an opposing surface opposite the contacting surface;
   wherein curvature of the opposing surface is a curvature selected from the group consisting of at least partially plano, at least partially concave, and at least partially convex.

38. The opthalmoscopic contact lens of claim 27, wherein curvature of the anterior reflecting surface is at least partially convex.

39. The opthalmoscopic contact lens of claim 38, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

40. The opthalmoscopic contact lens of claim 39, wherein the anterior reflecting surface and the refracting surface together comprise a continuous surface.

41. The opthalmoscopic contact lens of claim 39, wherein the opthalmoscopic contact lens is a doublet lens.

42. The opthalmoscopic contact lens of claim 41, wherein the doublet lens is a cemented doublet lens that includes
   an anterior portion; and
   a posterior portion that includes the contacting surface and an opposing surface opposite the contacting surface;
   wherein curvature of the opposing surface is a curvature selected from the group consisting of at least partially plano, at least partially concave, and at least partially convex.

43. The opthalmoscopic contact lens of claim 27, wherein curvature of the anterior reflecting surface is at least partially a polynomial-defined curvature that includes concave and convex attributes.

44. The opthalmoscopic contact lens of claim 43, wherein the anterior reflecting surface is a surface selected from the group consisting of a surface that is at least partially mirrored, a surface that reflects at least partially through total internal reflection, and a surface that is both at least partially mirrored and reflects at least partially through total internal reflection.

45. The opthalmoscopic contact lens of claim 44, wherein the anterior reflecting surface and the refracting surface together comprise a continuous surface.

46. The opthalmoscopic contact lens of claim 44, wherein the opthalmoscopic contact lens is a doublet lens.

47. The opthalmoscopic contact lens of claim 46, wherein the doublet lens is a cemented doublet lens that includes
   an anterior portion; and
   a posterior portion that includes the contacting surface and an opposing surface opposite the contacting surface;
   wherein curvature of the opposing surface is a curvature selected from the group consisting of at partially plano, at least partially concave, and at least partially convex.

48. A method for manufacturing an opthalmoscopic contact lens for viewing or treating structures within an eye, comprising the steps of:
   forming a contacting surface adapted for placement on a cornea of an eye and further adapted to permit entrance into the lens of light rays emanating from structures within the eye;
   forming an anterior reflecting surface positioned anterior of the contacting surface and adapted to reflect each of the light rays in a posterior direction as a positive reflection that is a first reflection in an ordered sequence of reflections;
   forming a posterior reflecting surface positioned posterior of the anterior reflecting surface and adapted to reflect each of the light rays in an anterior direction as a positive reflection that is a next reflection in the ordered sequence of reflections; and
   forming a refracting surface positioned anterior to the posterior reflecting surface and adapted to permit the light rays to pass through to form an inverted final real image of the structures.

49. The method of claim 48, wherein the step of forming a posterior reflecting surface includes shaping the posterior reflecting surface as at least partially concave.

50. The method of claim 49, wherein the step of forming a posterior reflecting surface includes at least partially mirroring the posterior reflecting surface.

51. The method of claim 50, wherein the step of forming an anterior reflecting surface includes shaping the anterior reflecting surface as at least partially plano.

52. The method of claim 51, wherein the step of forming an anterior reflecting surface includes at least one step selected from the group of steps consisting of at least partially mirroring the anterior reflecting surface, forming at least part of the anterior reflecting surface as a totally internally reflecting surface, and both partially mirroring the anterior reflecting surface and forming at least part of the anterior reflecting surface as a totally internally reflecting surface.

53. The method of claim 52, wherein the step of forming a contacting surface further comprises forming a posterior portion of a doublet lens that includes the contacting surface and an opposing surface positioned opposite the contacting surface.

54. The method of claim 53, wherein forming a posterior portion of a doublet lens includes shaping the opposing surface as at least partially plano, at least partially concave, or at least partially convex.

55. The method of claim 54, further comprising the step of cementing the posterior portion to an anterior portion of a doublet lens that includes the anterior reflecting surface and the refracting surface.

56. The method of claim 52, further comprising forming a continuous surface that includes both the anterior reflecting surface and the refracting surface.

57. The method of claim 50, wherein the step of forming an anterior reflecting surface includes shaping the anterior reflecting surface as at least partially concave.

58. The method of claim 57, wherein the step of forming an anterior reflecting surface includes at least one step selected from the group of steps consisting of at least partially mirroring the anterior reflecting surface, forming at least part of the anterior reflecting surface as a totally internally reflecting surface, and both partially mirroring the anterior reflecting surface and forming at least part of the anterior reflecting surface as a totally internally reflecting surface.

59. The method of claim 58, wherein the step of forming a contacting surface further comprises forming a posterior portion of a doublet lens that includes the contacting surface and an opposing surface positioned opposite the contacting surface.

60. The method of claim 59, wherein forming a posterior portion of a doublet lens includes shaping the opposing surface as at least partially plano, at least partially concave, or at least partially convex.

61. The method of claim 60, further comprising the step of cementing the posterior portion to an anterior portion of a doublet lens that includes the anterior reflecting surface and the refracting surface.

62. The method of claim 58, further comprising forming a continuous surface that includes both the anterior reflecting surface and the refracting surface.

63. The method of claim 50, wherein the step of forming an anterior reflecting surface includes shaping the anterior reflecting surface as at least partially convex.

64. The method of claim 63, wherein the step of forming an anterior reflecting surface includes at least one step selected from the group of steps consisting of at least partially mirroring the anterior reflecting surface, forming at least part of the anterior reflecting surface as a totally internally reflecting surface, and both partially mirroring the anterior reflecting surface and forming at least part of the anterior reflecting surface as a totally internally reflecting surface.

65. The method of claim 64, wherein the step of forming a contacting surface further comprises forming a posterior portion of a doublet lens that includes the contacting surface and an opposing surface positioned opposite the contacting surface.

66. The method of claim 65, wherein forming a posterior portion of a doublet lens includes shaping the opposing surface as at least partially plano, at least partially concave, or at least partially convex.

67. The method of claim 66, further comprising the step of cementing the posterior portion to an anterior portion of a doublet lens that includes the anterior reflecting surface and the refracting surface.

68. The method of claim 64, further comprising forming a continuous surface that includes both the anterior reflecting surface and the refracting surface.

69. The method of claim 50, wherein the step of forming an anterior reflecting surface includes shaping the anterior reflecting surface as at least partially curved in a manner that includes both concave and convex attributes as defined by a polynomial function.

70. The method of claim 69, wherein the step of forming an anterior reflecting surface includes at least one step selected from the group of steps consisting of at least partially mirroring the anterior reflecting surface, forming at least part of the anterior reflecting surface as a totally internally reflecting surface, and both partially mirroring the anterior reflecting surface and forming at least part of the anterior reflecting surface as a totally internally reflecting surface.

71. The method of claim 70, wherein the step of forming a contacting surface further comprises forming a posterior portion of a doublet lens that includes the contacting surface and an opposing surface positioned opposite the contacting surface.

72. The method of claim 71, wherein forming a posterior portion of a doublet lens includes shaping the opposing surface as at least partially plano, at least partially concave, or at least partially convex.

73. The method of claim 72, further comprising the step of cementing the posterior portion to an anterior portion of a doublet lens that includes the anterior reflecting surface and the refracting surface.

74. The method of claim 70, further comprising the step of forming a continuous surface that includes both the anterior reflecting surface and the refracting surface.

75. An opthalmoscopic contact lens for viewing or treating structures within an eye, comprising:
   means for contacting a surface of a cornea of an eye, the means for contacting a surface of a cornea adapted to permit entrance into the lens of light rays emanating from structures within the eye;
   anterior means for reflecting, positioned anterior of the means for contacting a surface of a cornea, adapted to reflect each of the light rays in a posterior direction as a positive reflection that is a first reflection in an ordered sequence of reflections;
   posterior means for reflecting, positioned posterior of the anterior means for reflecting, adapted to reflect each of the light rays in an anterior direction as a positive reflection that is a next reflection in the ordered sequence of reflections; and
   means for refracting positioned anterior to the posterior means for reflecting and adapted to permit the light rays to pass through to form an inverted final real image of the structures.

76. The opthalmoscopic contact lens of claim 75, wherein the structures are structures within an anterior chamber of the eye.

77. The opthalmoscopic contact lens of claim 76, wherein the posterior means for reflecting is at least partially concave.

78. The opthalmoscopic contact lens of claim 77, wherein the posterior means for reflecting is at least partially mirrored.

79. The opthalmoscopic contact lens of claim 78, wherein curvature of the anterior means for reflecting is at least partially plano.

80. The opthalmoscopic contact lens of claim 79, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

81. The opthalmoscopic contact lens of claim 80, wherein the anterior means for reflecting and the means for refracting together comprise a continuous surface.

82. The opthalmoscopic contact lens of claim 80, wherein the opthalmoscopic contact lens is a doublet lens.

83. The opthalmoscopic contact lens of claim 82, wherein the doublet lens is a cemented doublet lens that includes
an anterior portion; and
a posterior portion that includes the means for contacting and a surface opposite the means for contacting;
wherein curvature of the opposing surface is a curvature selected from the group consisting of at least partially plano, at least partially concave, and at least partially convex.

84. The opthalmoscopic contact lens of claim 78, wherein curvature of the anterior means for reflecting is at least partially concave.

85. The opthalmoscopic contact lens of claim 84, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

86. The opthalmoscopic contact lens of claim 85, wherein the anterior means for reflecting and the means for refracting together comprise a continuous surface.

87. The opthalmoscopic contact lens of claim 85, wherein the opthalmoscopic contact lens is a doublet lens.

88. The opthalmoscopic contact lens of claim 87, wherein the doublet lens is a cemented doublet lens that includes
an anterior portion; and
a posterior portion that includes the means for contacting and a surface opposite the means for contacting;
wherein curvature of the opposing surface is a curvature selected from the group consisting of at least partially plano, at least partially concave, and at least partially convex.

89. The opthalmoscopic contact lens of claim 78, wherein curvature of the anterior means for reflecting is at least partially convex.

90. The opthalmoscopic contact lens of claim 89, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

91. The opthalmoscopic contact lens of claim 90, wherein the anterior means for reflecting and the means for refracting together comprise a continuous surface.

92. The opthalmoscopic contact lens of claim 90, wherein the opthalmoscopic contact lens is a doublet lens.

93. The opthalmoscopic contact lens of claim 92, wherein the doublet lens is a cemented doublet lens that includes
an anterior portion; and
a posterior portion that includes the means for contacting and a surface opposite the means for contacting;
wherein curvature of the opposing surface is a curvature selected from the group consisting of at least partially plano, at least partially concave, and at least partially convex.

94. The opthalmoscopic contact lens of claim 78, wherein curvature of the anterior means for reflecting is at least partially a polynomial-defined curvature that includes concave and convex attributes.

95. The opthalmoscopic contact lens of claim 94, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

96. The opthalmoscopic contact lens of claim 95, wherein the anterior means for reflecting and the means for refracting together comprise a continuous surface.

97. The opthalmoscopic contact lens of claim 95, wherein the opthalmoscopic contact lens is a doublet lens.

98. The opthalmoscopic contact lens of claim 97, wherein the doublet lens is a cemented doublet lens that includes
an anterior portion; and
a posterior portion that includes the means for contacting and a surface opposite the means for contacting;
wherein curvature of the opposing surface is a curvature selected from the group consisting of at least partially plano, at least partially concave, and at least partially convex.

99. The opthalmoscopic contact lens of claim 75, wherein the structures are structures within a posterior chamber of the eye.

100. The opthalmoscopic contact lens of claim 99, wherein the posterior means for reflecting is at least partially concave.

101. The opthalmoscopic contact lens of claim 100, wherein the posterior means for reflecting is at least partially mirrored.

102. The opthalmoscopic contact lens of claim 101, wherein curvature of the anterior means for reflecting is at least partially plano.

103. The opthalmoscopic contact lens of claim 102, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

104. The opthalmoscopic contact lens of claim 103, wherein the anterior means for reflecting and the means for refracting together comprise a continuous surface.

105. The opthalmoscopic contact lens of claim 103, wherein the opthalmoscopic contact lens is a doublet lens.

106. The opthalmoscopic contact lens of claim 105, wherein the doublet lens is a cemented doublet lens that includes
an anterior portion; and
a posterior portion that includes the means for contacting and a surface opposite the means for contacting;
wherein curvature of the opposing surface is a curvature selected from the group consisting of at least partially plano, at least partially concave, and at least partially convex.

107. The opthalmoscopic contact lens of claim 101, wherein curvature of the anterior means for reflecting is at least partially concave.

108. The opthalmoscopic contact lens of claim 107, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

109. The opthalmoscopic contact lens of claim 108, wherein the anterior means for reflecting and the means for refracting together comprise a continuous surface.

110. The opthalmoscopic contact lens of claim 108, wherein the opthalmoscopic contact lens is a doublet lens.

111. The opthalmoscopic contact lens of claim 110, wherein the doublet lens is a cemented doublet lens that includes
   an anterior portion; and
   a posterior portion that includes the means for contacting and a surface opposite the means for contacting;
   wherein curvature of the opposing surface is a curvature selected from the group consisting of at least partially plano, at least partially concave, and at least partially convex.

112. The opthalmoscopic contact lens of claim 101, wherein curvature of the anterior means for reflecting is at least partially convex.

113. The opthalmoscopic contact lens of claim 112, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

114. The opthalmoscopic contact lens of claim 113, wherein the anterior means for reflecting and the means for refracting together comprise a continuous surface.

115. The opthalmoscopic contact lens of claim 113, wherein the opthalmoscopic contact lens is a doublet lens.

116. The opthalmoscopic contact lens of claim 115, wherein the doublet lens is a cemented doublet lens that includes
   an anterior portion; and
   a posterior portion that includes the means for contacting and a surface opposite the means for contacting;
   wherein curvature of the opposing surface is a curvature selected from the group consisting of at least partially plano, at least partially concave, and at least partially convex.

117. The opthalmoscopic contact lens of claim 101, wherein curvature of the anterior means for reflecting is at least partially a polynomial-defined curvature that includes concave and convex attributes.

118. The opthalmoscopic contact lens of claim 117, wherein the anterior means for reflecting includes a surface selected from the group consisting of a surface that is at least partially mirrored, a surface that reflects at least partially through total internal reflection, and a surface that is both at least partially mirrored and reflects at least partially through total internal reflection.

119. The opthalmoscopic contact lens of claim 118, wherein the anterior means for reflecting and the means for refracting together comprise a continuous surface.

120. The opthalmoscopic contact lens of claim 118, wherein the opthalmoscopic contact lens is a doublet lens.

121. The opthalmoscopic contact lens of claim 120, wherein the doublet lens is a cemented doublet lens that includes
   an anterior portion; and
   a posterior portion that includes the contacting surface and an opposing surface opposite the contacting surface;
   wherein curvature of the opposing surface is a curvature selected from the group consisting of at least partially plano, at least partially concave, and at least partially convex.

* * * * *